United States Patent [19]

Azain et al.

[11] Patent Number: 4,863,736

[45] Date of Patent: Sep. 5, 1989

[54] SOMATOTROPIN PROLONGED RELEASE

[75] Inventors: Michael J. Azain, Defiance; Kenneth E. Eigenberg, Ballwin; Thomas R. Kasser, Chesterfield; M. Jerome Sabacky, Ballwin, all of Mo.

[73] Assignee: Monsanto Company, St. Louis, Mo.

[21] Appl. No.: 146,381

[22] Filed: Feb. 3, 1988

Related U.S. Application Data

[63] Continuation-in-part of Ser. No. 26,095, Mar. 16, 1987, abandoned.

[51] Int. Cl.$^4$ .............................................. A61F 2/00
[52] U.S. Cl. ................................... 424/423; 424/424; 424/425; 424/426; 424/438
[58] Field of Search .......................... 424/438, 422-426

[56] References Cited

U.S. PATENT DOCUMENTS

| | | | |
|---|---|---|---|
| 2,517,513 | 8/1950 | Vaernet | 128/272 |
| 4,164,560 | 8/1979 | Folkman et al. | 128/260 X |
| 4,452,775 | 6/1984 | Kent | 514/772 X |
| 4,765,980 | 8/1988 | De Prince et al. | 424/108 |
| 4,786,501 | 11/1988 | Janski et al. | 424/422 |

FOREIGN PATENT DOCUMENTS

| | | |
|---|---|---|
| 193917 | 4/1986 | European Pat. Off. |
| 201219 | 11/1986 | European Pat. Off. |
| 204476 | 12/1986 | European Pat. Off. |
| 216485 | 4/1987 | European Pat. Off. |
| 246540 | 11/1987 | European Pat. Off. |
| 885798 | 12/1961 | United Kingdom |

OTHER PUBLICATIONS

Higgs, David A. et al., General and Comparative Endochrinology, vol. 27, pp. 240-253, 1975.

Higgs, David A. et al., Journal of Fisheries Research Board of Canada, vol. 33, pp. 1585-1603, 1976.

Davis, S. L. et al., *Continuous Elevation of Blood Growth Hormone Concentration by Beeswax Implant,* pp. 1980-1982, 1983.

*Primary Examiner*—Michael Lusignan
*Attorney, Agent, or Firm*—Jon H. Beusen; George R. Beck

[57] ABSTRACT

Provided is a shaped article adapted for parenteral implantation, to obtain prolonged administration of a somatotropin to an animal comprising an effective dose of a solid somatotropin, which is essentially binder-free, essentially matrix-free and has at least one uncoated release surface.

48 Claims, 3 Drawing Sheets

SOMATOTROPIN PROLONGED RELEASE

This is a continuation-in-part of copending Application Ser. No. 26,095, filed Mar. 16, 1987, now abandoned.

This invention relates to prolonged release of somatotropins, more particularly to shaped articles suitable for parenteral administration of somatotropins, and to methods of administering somatotropins by parenteral implantation of such shaped articles.

BACKGROUND OF THE INVENTION

Somatotropins are known to be effective at enhancing growth, feed efficiency, milk production, and fat-to-lean ratio of various animals when parenterally administered to augment the level of somatotropin normally produced by the animal. While these objectives can sometimes be met with daily injections of somatotropins, prolonged release systems are easier to administer, and sometimes give superior results due to a more constant blood concentration.

A variety of methods have been used in the prior art to achieve prolonged release of somatotropins. Somatotropin has been dispersed in a biocompatible oil, optionally in the presence of an antihydration agent (see European Patent Application Publication No. 177,478, published Apr. 9, 1986). Somatotropin has been complexed with a water-soluble or water-dispersible carbohydrate polymer, such as dextrin, dextran, and various bean gums. This complex is administered parenterally as a solution, dispersion or paste (see European Patent Application No. 193,917 published Sept. 10, 1986). And, somatotropin has been formulated with cholesterol and compressed to form a matrix implant (see U.S. Pat. No. 4,452,775, to Kent, issued June 5, 1984).

A large number of systems are known for parenteral implantation of articles to release a variety of bioactive materials. A wide variety of binders and matrix agents are known in the art for use along with bioactive materials to produce articles for parenteral implantation. Similarly, it is known to implant coated articles in which release of a bioactive core material is regulated by diffusion through or erosion of a polymeric coating. These prior art systems have one thing in common. In each, release of the active substance is regulated by the matrix agent, the binder or the coating. Release is accomplished by transfer through or erosion of the matrix agent, binder or coating. Prolonged release of somatotropins has followed a similar pattern, where dissolution of the active somatotropin is inhibited by another substance and release is regulated by that other substance.

The current invention provides for parenteral administration of a somatotropin without the need for another substance to control release of the somatotropin. Prior to this invention, it has not been known in the art to parenterally administer a somatotropin in the form of a shaped article which is substantially matrix-free, substantially binder-free, and with at least one uncoated release surface.

SUMMARY OF THE INVENTION

This invention provides a novel and useful delivery system for parenterally administering a somatotropin to an animal, by parenteral implantation of a shaped article comprising an effective dose of a solid somatotropin, which is essentially binder-free, essentially matrix-free, and has at least one uncoated release surface. In another aspect, the current invention is a shaped article for parenteral administration of a somatotropin to an animal, consisting essentially of a solid somatotropin, optionally an effective amount of a lubricant and optionally a coating on one or more surfaces, but with at least one uncoated release surface. As used herein, the phrase "consisting essentially of" means that the article does not contain any components that act as a matrix agent or a binder, as each of those terms is defined below. The current invention also provides a method of administering a somatotropin by parenteral implantation of these shaped articles.

DETAILED DESCRIPTION OF THE INVENTION

Figure 1:
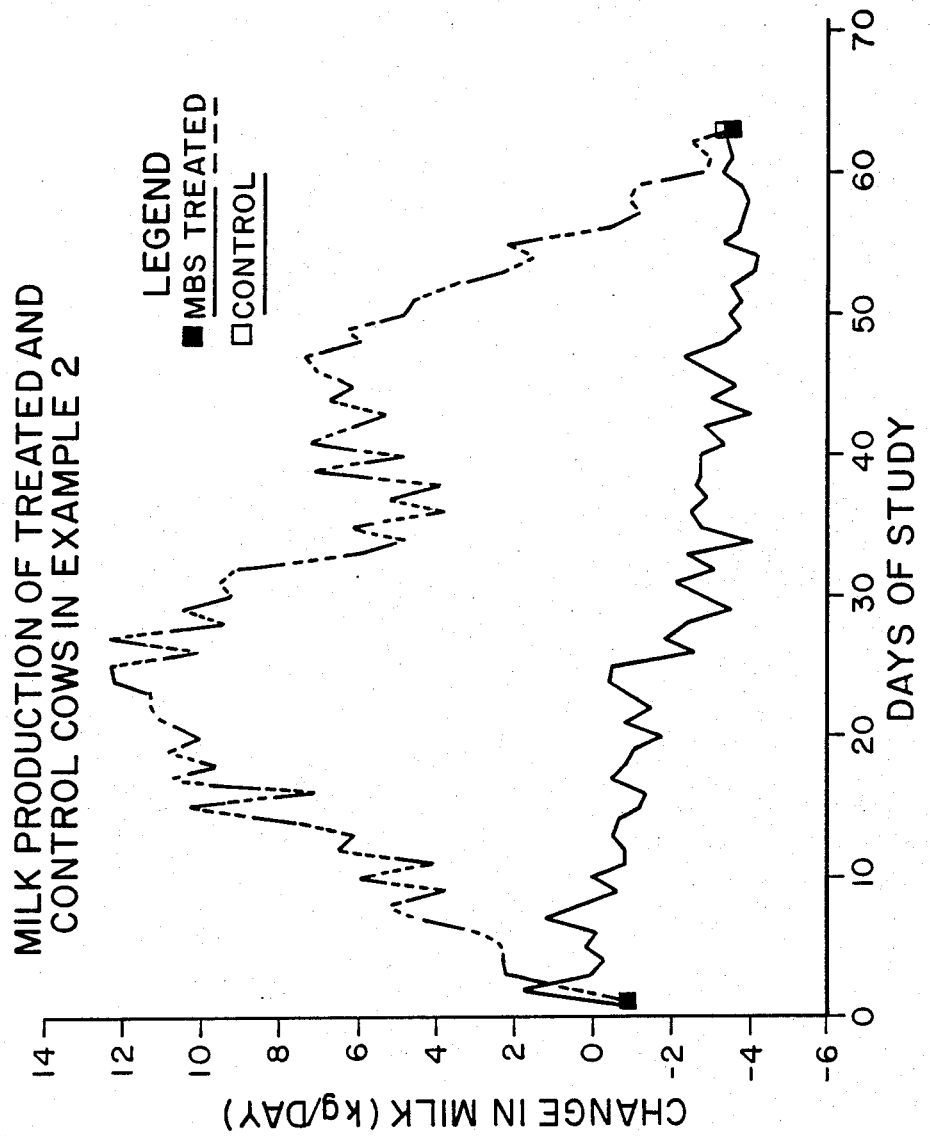
FIG. 1 graphically represents the milk production of treated and control cows in Example 2.

As used in the specification and claims, the following words have the following meanings:

The term "matrix" means a solid phase carrier, also referred to as a "matrix agent", which forms a network within which particles of the somatotropin are dispersed and thereby inhibits dissolution of the somatotropin. The release of the somatotropin is regulated by erosion of the matrix agent or by diffusion of the somatotropin through passages in the matrix agent network.

The term "binder" refers to polymeric materials, either of synthetic or biological origin, which are used to increase adhesion between particles of the somatotropin, or between particles of the somatotropin and a matrix agent.

The phrases "essentially binder-free" and "essentially matrix-free" mean that the shaped article does not contain a sufficient quantity of binder or matrix agent to have a substantial effect on release of the somatotropin.

The phrase "at least one uncoated release surface" means that at least a portion of the surface of the article does not have a coating which materially inhibits release of the somatotropin. This uncoated release surface may be an entire face of the article, e.g. one or both ends of a cylindrical article, or may be an uncoated area of a larger surface of the article, e.g. one or more uncoated areas on a spherical article, or one or more uncoated areas on the curved surface of a cylindrical article.

The term "somatotropin" means a polypeptide that has biological activity and chemical structure similar to those of a somatotropin produced in the pituitary gland of an animal. Such somatotropin includes natural somatotropin produced by pituitary somatotropic cells, and alternatively, somatotropin produced by recombinant DNA techniques by which somatotropin is expressed by genetically transformed cells. Suitable systems include tissue culture of transformed tissue cells, and expression by transformed microbes such as *E. coli*, other bacteria, yeast, etc. Due to production considerations, it is preferred to use microbially expressed somatotropin. Such recombinant DNA produced somatotropin may have an amino acid sequence identical to a naturally occurring somatotropin as well as variants in which amino acid residues are either added to, subtracted from or are different from the amino acid sequence of the naturally occurring somatotropin, provided that such additions, deletions or changes in the amino acid sequence do not intolerably adversely affect bioactivity of the somatotropin. Also included are somatotropins which are salts or complexes with anions or cations. These complexes can be coprecipitated or lyophilized in the presence of an inorganic or organic compound, such as a salt, to form an intimate mixture or can be formed by wetting of a dry blend of the somatotropin and a compound containing the desired ion. Mixtures of somatotropins or multiple layered somatotropins are also included.

Examples of somatotropins useful with the current invention include avian somatotropin for treating chickens, turkeys and the like; mammalian somatotropins for treating humans, cattle, swine, sheep, goats and the like; and aquatic somatotropin for treating fish and the like. Particularly useful are bovine somatotropin and porcine somatotropin.

Because of the ability to produce substantial quantities of somatotropin, it is preferred to use recombinant DNA techniques to microbially express the somatotropin. Additionally, recombinant DNA techniques allow for production of variants, that are either similar to or different from the sequences of the naturally occurring somatotropins. The sequences for naturally occurring bovine and porcine somatotropins are given in Seeburg, et al., DNA, Vol. 2, No. 1 pp. 37–45(1983), which is incorporated herein by reference. In the variants below, the N-methionine can sometimes be removed during or after expression.

Examples of bovine somatotropin variants include, but are not limited to, polypeptide having the following amino acid sequences with unspecified amino acid residues being similar to the naturally occurring somatotropin:

| | | | | |
|---|---|---|---|---|
| NH$_2$—met—phe(1)—pro(2) | ... | leu(126) | ... | phe(190)—COOH |
| NH$_2$—met—phe(1)—pro(2) | ... | val(126) | ... | phe(190)—COOH |
| NH$_2$—ala—phe(1)—pro(2) | ... | val(126) | ... | phe(190)—COOH |
| NH$_2$—ala—phe(1)—pro(2) | ... | leu(126) | ... | phe(190)—COOH |
| NH$_2$—phe(1)—pro(2) | ... | leu(126) | ... | phe(190)—COOH |
| NH$_2$—phe(1)—pro(2) | ... | val(126) | ... | phe(190)—COOH |
| NH$_2$—met—asp—glu—phe(1)—pro(2) | ... | leu(126) | ... | phe(190)—COOH |
| NH$_2$—met—asp—glu—phe(1)—pro(2) | ... | val(126) | ... | phe(190)—COOH |
| NH$_2$—met(4)—ser(5) | ... | leu(126) | ... | phe(190)—COOH |
| NH$_2$—met(4)—ser(5) | ... | val(126) | ... | phe(190)—COOH |

As can be seen from the above, these variants optionally may have a methionyl residue at the N-terminus. The first variant in the list above, with a methionyl residue at the N-terminus, and a leucyl residue at position 126 is referred to herein as methionyl bovine somatotropin or "MBS", and the third variant in the list above, with an alanyl residue at the N-terminus and a valyl residue at position 126 is referred to as alanyl-valyl bovine somatotropin or "ala-val BST".

Examples of porcine somatotropin variants include, but are not limited to, polypeptides having the following amino acid sequences, with unspecified amino acid residues being similar to the naturally occurring somatotropin:

| | | |
|---|---|---|
| NH$_2$—ala—phe(1) | ... | phe(190)—COOH |
| NH$_2$—met—phe(1) | ... | phe(190)—COOH |
| NH$_2$—met(4)—pro(5) | ... | phe(190)—COOH |

| | |
|---|---|
| -continued | |
| NH$_2$—met(6)—ser(7) ... phe(190)—COOH | |

The first variant in the list above, with an alanyl residue at the N-terminus is referred to herein as alanyl porcine somatotropin or "APS". The second variant in the list above is referred to herein as methionyl porcine somatotropin or "MPS".

While use of somatotropin variants can in some circumstances be useful and advantageous, care should be taken so that the variant does not differ from the naturally occurring somatotropin to the extent that bioactivity is intolerably adversely affected or that the variant triggers intolerable production of undesirable antibodies.

In order to be biologically active, the somatotropin must be natured, i.e., to have a folded structure resulting in biological activity. While it is preferable to minimize the presence of inactive polypeptide and inactive polypeptide aggregate, some amounts may be present, provided they do not intolerably inhibit activity of the bioactive somatotropin.

In the prior art, release of somatotropin from a prolonged release system has been regulated by a mechanism involving another component of the system, e.g., erosion of a matrix, etc. In the current invention, release of the somatotropin is regulated by the properties of the somatotropin itself and can also be affected to some degree by such factors as the size and shape of the article and by the process of its production.

The properties of the somatotropin that most effect the release characteristics are its solubility and its rate of dissolution. This combination of properties will be referred to as "intrinsic dissolution". The intrinsic dissolution, and some other properties, of the somatotropin can be manipulated in a number of ways. Different somatotropin variants often have somewhat different solubilities and/or rates of dissolution, and as a result intrinsic dissolution can sometimes be manipulated to some extent by choice of a variant. The method of isolation of the solid somatotropin, e.g. pH of precipitation of a precipitated somatotropin or lyophilization conditions of solution lyophilized somatotropins can also affect intrinsic dissolution somewhat. The intrinsic dissolution can also be manipulated by use of a somatotropin that is associated with another ion or with another compound such as a salt. The actual structure of this type of association is not clear, but they are believed to be salts, complexes, intimate mixtures formed by coprecipitation, or some combination of these three forms. In this specification and claims, when it is desired to refer to a somatotropin which is associated with a particular ion or a particular salt, it will be referred to, for instance, as a zinc-associated bovine somatotropin, copper-associated porcine somatotropin, or sodium bicarbonate-associated bovine somatotropin. When referred to generally, it will simply be referred to as an associated somatotropin.

Associated somatotropins can be formed with nontoxic amounts of various cations, including both monovalent metals and polyvalent metals. Examples of suitable monovalent metals include sodium, potassium, and the like. Examples of suitable polyvalent metals include zinc, iron, calcium, bismuth, barium, magnesium, manganese, aluminum, copper, cobalt, nickel, cadmium and the like. However, particularly with polyvalent metals which can under some circumstances be toxic, care should be taken to use nontoxic quantities. Associated somatotropins can also be formed with anions, such as bicarbonate, acetate, glycine, borate and the like. Combinations of cations, anions and other compounds may also be used. The ratio of cation, anion or other compound to somatotropin may vary depending upon the conditions and the somatotropin used. Some or all of the ions may be associated in a salt of one of the amino acids in the somatotropin, may be occluded within folds or crystals of the somatotropin, may be associated as an ionic bridge between at least two somatotropin molecules, may be associated as a complex with the somatotropin, or may be associated in some other fashion.

Examples of other associated somatotropins include (a) acid addition salts formed with inorganic acids, such as hydrochloric, hydrobromic, sulfuric, phosphoric or nitric acids; or with organic acids such as acetic, oxalic, tartaric, succinic, maleic, fumaric, gluconic, citric, malic, ascorbic, benzylic, tannic, pamoic, alginic, polyglutamic, naphthalene sulfonic, naphthalene-disulfonic or polygalacturonic acids; (b) salts with polyfunctional organic compounds such as N,N'-dibenzylethylenediamine or ethylenediamine or procaine; or (c) combinations of two or more of the aforementioned types of salts such as zinc tannate.

Many of the benefits of associated somatotropins can be achieved by mixing the powdered somatotropin with a salt of the desired cation or anion or with the desired compound, prior to formation of the article. It is believed that the associated somatotropin forms in situ, during formation of the article, or after administration of the article to the animal.

If the associated somatotropin is relatively less soluble, it can be produced by adding the desired water-soluble salt or a water-soluble compound of the desired ion to a solution of the somatotropin, at the desired pH, to precipitate the desired associated somatotropin. For example, zinc-associated bovine or porcine somatotropin can be produced by addition of a water soluble zinc salt to an aqueous solution of the somatotropin buffered with a suitable buffering agent. The pH is preferred to be from about 9 to about 9.5.

If the associated somatotropin is relatively more soluble, it can be produced by lyophilization of a solution of the somatotropin with the desired salt or the desired ions. This solution can be produced by multiple dialysis or diafiltration of, for example, a urea solution to exchange urea with the desired salt, followed by dialysis or diafiltration with water to reduce the salt concentration to the desired level. For example, sodium bicarbonate-associated bovine somatotropin can be produced by diafiltration or dialysis of a urea solution of the somatotropin to achieve complete exchange of urea, with a sodium bicarbonate solution, followed by further diafiltration with water to remove excess sodium bicarbonate, followed by lyophilization to produce the sodium bicarbonate-associated somatotropin.

Somatotropins are often processed and purified in a buffer solution, such as sodium bicarbonate. It is preferred to adjust the concentration of the sodium bicarbonate by dialysis or diafiltration to the desired concentration. The pH can be maintained in a range in which the somatotropin is soluble by addition of a base, such as NaOH, to the dialysis water or to the somatotropin solution. The somatotropin can then be recovered by a number of means, such as by adjustment of the pH with a suitable acid, such as HCl, to precipitate the somatotropin followed by diafiltration and lyophilization or by direct lyophilization of the somatotropin solution. It is preferred that the somatotropin produced in this manner have a concentration of the buffer salt, e.g. sodium bicarbonate, from about 0% to about 20%, more preferably from about 0% to about 5%, and most preferably about 1% or less. A higher concentration of sodium bicarbonate increases intrinsic dissolution of the somatotropin, resulting in a product useful for release over a shorter time frame. A lower concentration of sodium bicarbonate, conversely, results in a product useful for release over a longer time frame. In this manner, the product can be designed for the desired time frame.

Another method of preparing the somatotropin is to isolate and purify the somatotropin, which is typically done under alkaline conditions, followed by dialysis to remove some of the buffer, and addition of an acid, such as phosphoric acid to produce an acidic solution of the somatotropin. The somatotropin can then be recovered from this acidic solution, for example, by addition of a base to raise the pH of the solution to a point where the somatotropin will precipitate. Care should be taken in using this procedure, to ensure that the pH is not reduced so far that the somatotropin is denatured.

Porcine somatotropin has an intrinsic dissolution that is somewhat higher than bovine somatotropin. For this reason, it is preferred to use a copper-associated porcine somatotropin. This copper-associated porcine somatotropin may contain from about 0.1% copper to about 3% copper, preferably from about 0.1% copper to about 2% copper and more preferably from about 0.1% copper to about 1% copper. A particularly preferred copper-associated porcine somatotropin has about a 1:1 mole ratio of copper to somatotropin, which represents about 0.3% copper. Copper-associated porcine somatotropin provides enhanced prolonged release and improved delivery efficiency of the porcine somatotropin. Additionally, there is some indication that copper-associated porcine somatotropin has a reduced tendency to form dimer and other aggregates, particularly after administration to the animal. The preferred variant is APS.

Many of the benefits of a precipitated copper-associated porcine somatotropin can be achieved by use of a physical mixture of the porcine somatotropin with the appropriate amount of a copper salt. When dry blends are used, additional copper salt should be added to the composition, over and above the amount required to produce a copper-associated somatotropin with the desired properties. For instance, a dry blend of copper salt and porcine somatotropin with a 2:1 mole ratio of copper to somatotropin will have release characteristics similar to a precipitated copper-associated porcine somatotropin having a 1:1 mole ratio. It is believed the copper-associated porcine somatotropin forms in situ during compaction or, more likely, after administration.

Release of the somatotropin can also be manipulated by control of the release geometry of the article. This can be done, for instance, by choice of the size and shape of the article or by occlusion of a portion of the total surface area of the article with a coating. Both of these techniques are discussed below.

The shaped somatotropin articles of this invention can be prepared using conventional techniques, such as compaction, spray drying accretion, prilling techniques, molding a moist paste and drying the molded article, and the like. Because compaction is the most commonly utilized method for formation of parenteral implants, and for the sake of simplicity, the current invention will be discussed in terms of formation by compaction.

The current invention may be produced in a conventional tabletting machine utilizing dies of appropriate size and shape and utilizing pressure within conventional ranges. Conventional handling and tabletting procedures can be used; for instance, the somatotropin can be precompacted and comminuted to improve handling characteristics and flowability.

Performance can be improved by careful choice of size and shape of the article. The article can be cylindrical, spherical, egg-shaped, or any other convenient shape. In order to maximize the time period over which the release occurs, it is preferable to utilize a shape which has a minimum surface area for a given dosage. If a single article is used, this can be accomplished by producing a spherical implant, or by producing a cylindrical implant in which the height of the cylinder is approximately equal to its diameter. However, other shapes and sizes can be used if shorter time periods are desired and for a number of other reasons. For instance, it is also advantageous to produce an article which can be administered using conventional devices used for parenteral administration of pellets or tablets. If these "implant guns" are being used, it is preferred that the shaped article of the current invention be a cylinder and have a diameter between about 1 mm and about 5 mm and a length between about 1 mm and about 25 mm. However, diameters from about 0.5 mm to about 12 mm and lengths from about 1 mm to about 50 mm, and even sizes outside these ranges can be used, if desired. If the size or shape of the article or the site of administration require, it is also possible to perform surgical implantation. Multiple articles can be implanted, if the desired dose is too large to be conveniently administered in one article, or if desired for some other reason, such as greater flexibility of dose.

It is preferred that the intrinsic dissolution and the area of the release surface be manipulated to achieve an average daily release rate over the effective duration of the article in the desired range. For dairy applications, the average daily release rate can be from about 1 mg to about 75 or even 100 mg per day, preferably from about 3 mg to about 50 mg per day and more preferably from about 6 mg to about 40 mg per day. For hog applications, the average daily release rate can be from about 0.5 mg to about 25 or even 30 mg per day, preferably from about 1 mg to about 20 mg per day, more preferably from about 2 mg to about 15 mg per day. Average daily release rates outside of these ranges can sometimes be useful, depending upon the desired result. The total dose of somatotropin should be sufficient to sustain the desired release rate for the desired time periods as discussed below.

The total dose of somatotropin is related to a large number of factors, such as size of the animal, the effect for which the somatotropin is being administered, the time period over which the dose is intended to last, and the like. As used in this specification and claims, an effective dose is a dose of bioactive somatotropin, either contained in one article or in multiple articles designed to be administered together, which is effective to achieve the desired effect over a prolonged period of time, sometimes as short as 1 or 2 days, but more often greater than about 7 days, in some circumstances up to about 28 days or even up to about 48 days or more.

For purposes of administration of somatotropin to cows, to enhance milk production, it is preferred that the dose be from about 5 mg to about 1000 mg or 1500 mg or more, more preferably from about 100 mg to about 800 mg, and that it be administered at intervals of about 1 day to about 28 days or longer or more preferably from about 7 days to about 28 days. For administration of porcine somatotropin to gestating sows and to lactating sows, it is preferred that the dose be from about 5 mg to about 225 mg or more, more preferably from about 75 mg to about 150 mg and that it be administered at intervals of about 1 day to about 28 days, preferably about 7 days to about 21 days. For administration to slaughter hogs to enhance weight gain and feed efficiency or to improve the fat-to-lean ratio, it is preferred that the doses be from about 10 mg to about 200 mg or more, more preferably from about 10 mg to about 90 mg, and that it be administered at intervals of about 7 days to about 60 days, preferably about 14 days to about 42 days or, for finishing hogs, it may be desirable to administer a dose about 7 days to about 60 days before slaughter. Administration at more frequent intervals to finishing hogs can be advantageous, particularly toward the end of finishing. This can allow greater flexibility in the administration schedule to more closely coincide with the time for slaughter of the animal. However, more frequent or less frequent administration can be effectively utilized in some circumstances and larger or smaller doses can also be effectively utilized under appropriate circumstances.

The amount of pressure utilized in forming a compacted somatotropin article is not critical, however, performance can be manipulated somewhat by careful choice of pressure. Sufficient pressure must be used to produce an article with sufficient strength and integrity so that it can withstand handling and implantation.

An additional method of controlling release rate is by occluding a portion of the total surface area of the article, to reduce the amount of surface from which dissolution occurs.

A coating may be used to substantially inhibit or to nearly completely halt release of the somatotropin from some surfaces of the object, to control the geometry of the release surface, for example, to maintain a constant area of the release surface. This can assist in attaining prolonged zero-order release of the somatotropin from the uncoated release surface, which is the primary release surface. For instance, the somatotropin article of the current invention may be a cylinder with a coating on the curved surface of the cylinder and no coating on one or both of the ends. In this way, as the somatotropin is released, and the article erodes, the area of the release surface remains relatively constant, rather than decreasing as would occur if release were to occur from all surfaces of the cylinder. Additionally the coating may cover most of the article, except one or more release "windows", which maintain a fairly constant release area over time.

To maximize this type of effect, for instance, for a cylindrical article coated on the entire curved surface, it is preferred that the coating substantially inhibit release of the somatotropin along the coated surface, and that the coating remain intact on the remaining curved surface of the cylinder as release occurs from the uncoated end(s). The coating may also erode from one or both ends as the somatotropin erodes. It is preferred that the coating maintain its effectiveness throughout a substantial majority of the life of the article after administration. However, useful results can be achieved with any coating that provides at least substantial inhibition of release of the somatotropin, provided that the primary release surface must be uncoated. It may also be preferable, particularly if the animal is to have repeated administration of somatotropin, that the coating eventually be absorbed by the animal and, of course, the coating must be biocompatible. Examples of substances that can be used to provide such a partial coating for a somatotropin article include, but are not limited to shellac, beeswax, cellulose acetate butyrate, polylactic acid, ethyl cellulose, silicones, ethylene vinyl acetate copolymer, hydroxy propyl cellulose, polycarbonate, polycaprolactone, cellulose acetate, polymethyl methacrylate and a variety of other polymers known for use as barrier coatings.

A similar result can be achieved by producing an article with an outside layer, for instance on the curved surface of a cylindrical article, of a relatively less soluble associated somatotropin, such as a zinc-associated somatotropin.

A temporary protective covering may be useful with the current invention. It may be advantageous to provide the somatotropin article with a light covering to protect the article during storage and handling, and possibly to be of assistance in administration of the article to the animal. In order for this type of covering to be useful with the current invention, the covering would either have to be removed prior to administration to the animal, such as by a brief soaking or washing procedure, or would be removed from the article very quickly upon administration to the animal. This temporary, protective covering would have very minimal effect on controlling release of the somatotropin, and after removal of the covering, the article will release somatotropin from at least one uncoated release surface. Because this type of covering has little or no effect on release, it is not considered to be a "coating" for purposes of this specification and claims. This temporary, protective covering could also be used along with the more permanent coating discussed above. This protective covering could simply be a much thinner application of the coating materials discussed above, provided that this much thinner coating must be quickly removed from the article, either before or immediately after implantation, or could be a covering that is quickly removed from the article, for instance because of its solubility, because it melts at body temperature, a combination of solubility and melting temperature or for some other reason. Suitable materials for this type of covering include, but are not limited to: polyvinyl alcohol, sugars, polyethylene glycol (such as PEG 8000), and other substances.

In addition to the somatotropin and the optional coating and optional protective covering outlined above, it may be advantageous to include other substances in the composition of the article of the current invention. Examples are lubricants, bacteriostats, antioxidants, antiinflammatory agents, antibiotics and the like. Conventional lubricants can be used to assist in the compaction process. Examples of such lubricants include stearates, such as magnesium stearate, palmitates, such as sodium palmitate, and other conventional lubricants. The amount of lubricant present should be sufficient to enable the somatotropin to flow freely and easily into the die and to enable the article to be easily removed from the die without damage to the article. However, the lubricant should not be present in quantities sufficient such that it acts as a matrix agent, or in some way intolerably adversely affects release of the somatotropin. For instance, magnesium stearate has little or no effect on release of the somatotropin up to a concentration of about 10%. When used in concentrations exceeding 30–50%, magnesium stearate significantly inhibits release of the somatotropin from the article. Similarly, sodium palmitate has little or no effect on release of the somatotropin up to a concentration of about 3%. When used in concentrations exceeding about 10%, sodium palmitate significantly or totally inhibits release. The effect of concentrations between these specified concentrations can be determined by routine testing. Similarly, effective concentration ranges for other conventional lubricants can be determined by simple procedures.

Other ingredients such as antioxidants, antiinflammatory agents, bacteriostats, antibiotics, agents to inhibit aggregation of the somatotropin, and the like may be included using conventional techniques. However, these ingredients also should not be present to such an extent they act as matrix agents or in other ways intolerably adversely affect release of the somatotropin. These effective concentrations can be determined in a similar manner to the procedure used for lubricants as discussed above. In some circumstances irradiation may be used to enhance sterility, however, care should be taken since radiation can, in some circumstances, reduce bioavailability of the somatotropin.

It may be advantageous for some somatotropins, to adjust the amount of water present in the somatotropin, either by careful control of drying techniques, such as lyophilization, or by allowing lyophilized somatotropin to be exposed to an atmosphere containing water vapor, until the desired amount of water is present in the composition. However, these adjustments should not be carried out under conditions that promote denaturation of the somatotropin, aggregate formation, or other degradation of the somatotropin or of its effectiveness. This can be accomplished either before or after formation of the article, and can be accomplished by other techniques.

The article of this invention can be administered in conventional manner, either subcutaneously, in the fatty tissues, or intramuscularly. They can be administered either surgically or utilizing conventional implantation devices.

The following examples illustrate the current invention, and are not intended as limiting. All parts and percentages are by weight, unless specified otherwise.

EXAMPLE 1

Microbially expressed MBS was prepared by expression of recombinant DNA essentially as described in Example A of European Patent Application No. 177,478, published Apr. 9, 1986, which is incorporated herein by reference. The refractile bodies were isolated by disruption of the cells, followed by centrifugation.

The refractile bodies were then solubilized, folded and oxidized in a solution of urea and trishydroxymethyl amino methane (TRIS) buffer. The buffered MBS solution was passed through a chromatography column containing DE-52 ion exchange resin. The concentration of this solution was adjusted to 22 mg/ml of MBS in a solution of 4.5M urea and 50 mM of trishydroxymethyl amino methane (TRIS) buffer at a pH of 9.3-9.5. This solution was sterile filtered through a 0.22 micron filter cartridge. The filtered solution was dialized against a 7-fold volume of 25 mM sodium bicarbonate buffer (at pH 9.5), replacing the buffer solution 8 times once every 8-12 hours. Then, the buffer solution was replaced with WFI-grade water, changed every 8-12 hours. As the pH dropped to 8-8.5, the MBS began to precipitate from solution. Dialysis was continued for an additional 4-6 changes with water, to further reduce the concentration of residual buffer components, until the pH was in the range of 6.5-7.5. The precipitated MBS was then lyophilized and recovered as a dry white powder. MBS prepared in this manner was used to prepare compacted somatotropin articles for parenteral implantation in lactating dairy cattle, as described below.

EXAMPLE 2

Compacted somatotropin articles were prepared from the MBS prepared as in Example 1. 50 mg of this MBS was placed into a tabletting die with a diameter of 6.4 mm and compressed in a Carver Model-C 12 Ton tabletting press with a hydraulic ram having an area of 21.25 sq. cm (3.294 sq. in.), at an applied load of 17,790 newtons (4000 lbs) as read from the gauge. Ten of these 50 mg compacted articles were surgically implanted subcutaneously in the postscapular region in 8 lactating Holstein cows on day 0, day 14, and day 28. A total of 30 compacted articles were implanted in each of the treated cows. Milk production of the treated cows over a period of 56 days was compared to a group of 9 control cows that received no somatotropin. The increase in production of milk and 3.5% fat corrected (3.5 FC) milk of the treated cows over the untreated cows is summarized in Table I and shown graphically in FIG. 1.

TABLE I

| Days | Increase in Actual Milk (kg/day) | Incresse in 3.5 FC Milk (kg/day) | % Increase in FC Milk Over Control |
|---|---|---|---|
| 1-14 | 3.7 | 4.1 | 14.7% |
| 15-28 | 11.6 | 11.9 | 43.4 |
| 29-42 | 9.6 | 9.6 | 34.9 |
| 43-49 | 9.5 | 10.6 | 39.1 |
| 50-56 | 6.3 | 5.1 | 19.2 |

Figure 2:
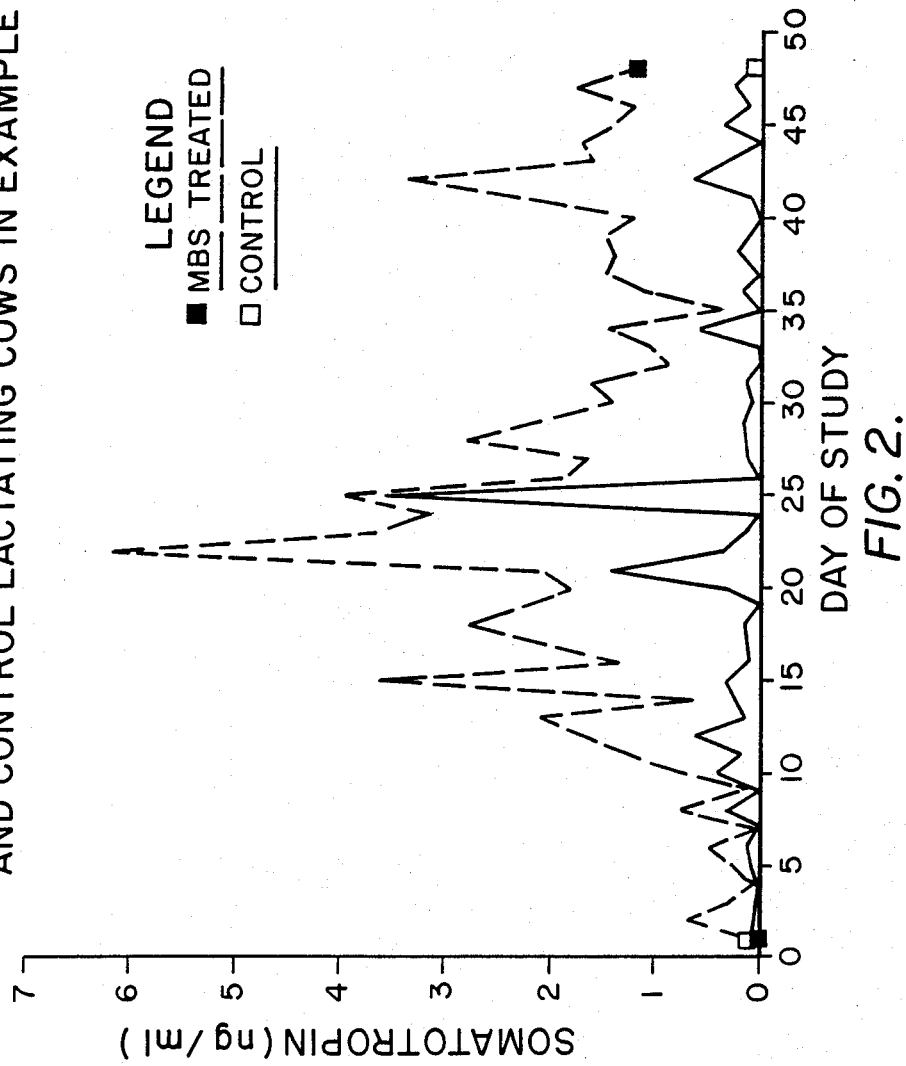
FIG. 2 graphically represents the serum somatotropin concentration of treated and control cows in Example 2.

Blood samples were taken daily throughout the study and the blood serum was analyzed by radioimmunoassay (RIA) for somatotropin. The serum levels determined are shown graphically in FIG. 2. Milk production was consistent with the observed serum somatotropin profile.

EXAMPLE 3

Figure 3:
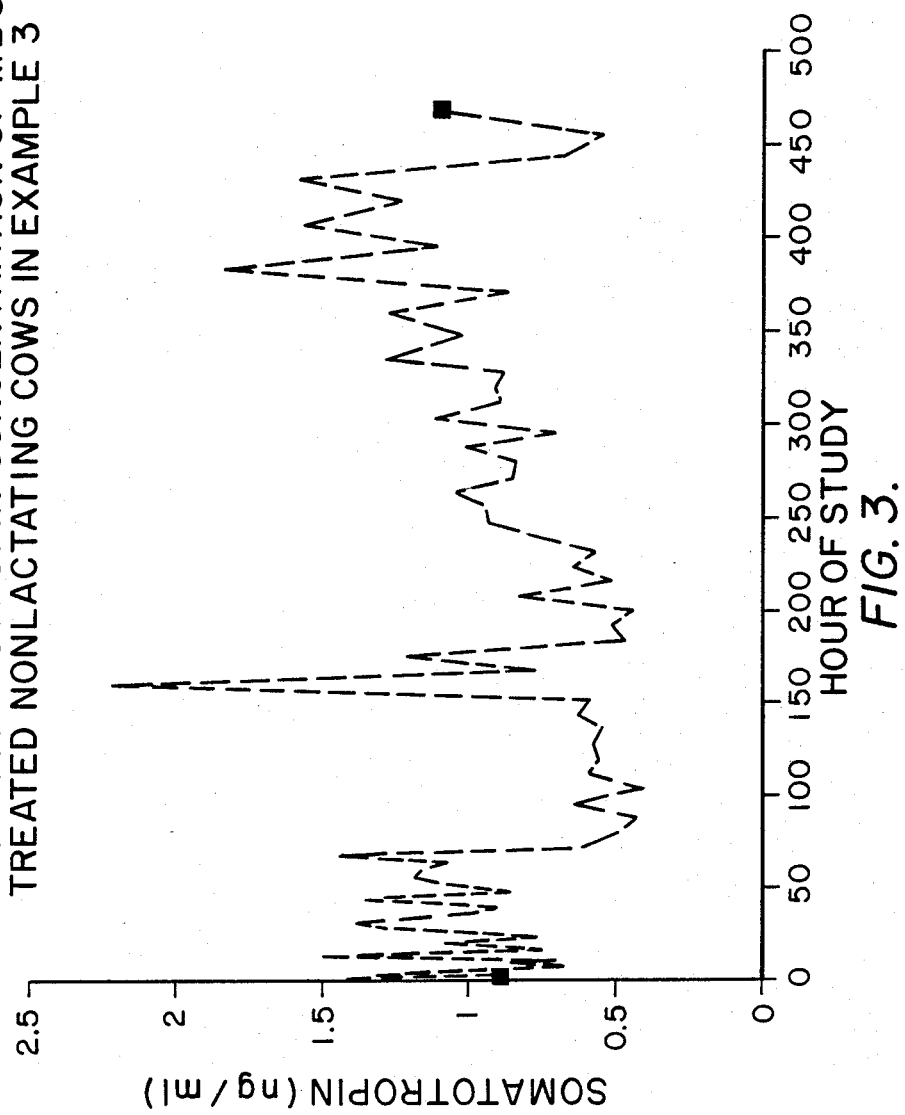
FIG. 3 graphically represents the serum somatotropin concentration of MBS treated nonlactating cows in Example 3.

A group of 14 nonlactating Holstein cows were divided into two groups of 7. One group received surgical implantation as described in Example 2, of ten of the 50 mg MBS articles prepared as described in Example 2, and the other group received sham surgical procedures. Ten blood samples were taken throughout day 1, 6 samples on days 2 and 3, 3 samples on days 4 through 14 and 2 samples on days 15 through 21. Blood serum somatotropin level was determined by RIA, and the results are shown in FIG. 3. The serum levels in this study were somewhat lower than in the lactation study in Example 3. The reason for this lower level is not understood, but it is believed that it may be related to normal fluctuations in natural somatotropin production. However, a steady elevation lasting 17 or 18 days was observed.

EXAMPLE 4

Five of the 50 mg MBS articles prepared as described in Example 2 were surgically implanted into 5 nonlactating Holstein heifers either the right or left anterior or posterior postscapular region on days 0, 3, 7 and 14 of the study. On day 14, the animals were sacrificed, and tissue analysis was done. Undue adverse tissue reaction was not observed, indicating good biocompatibility.

EXAMPLE 5

Microbially expressed APS was prepared by expression of recombinant DNA substantially as described in Example 3B of European Patent Application No. 193,515 published Sept. 3, 1986, which is incorporated herein by reference. The APS refractile bodies were isolated, solubilized, natured and purified as described in Example 1 through the ion exchange step. The APS buffered solution was dialized against a sodium bicarbonate buffer solution, and the resulting bicarbonate buffered solution was sterile filtered and lyophilized. This material is referred to in the Examples as "APS bulk powder". 5.4 g of this APS was dissolved in 250 ml of deionized water and dialized against 4 changes of 16 volumes of water over 24 hours at 4° C. The dialized APS was precipitated at pH 6-8 with 350 $\mu$moles of a 100 mM copper sulfate solution. The precipitate formed by addition of copper sulfate was isolated by centrifugation and was lyophilized. The resulting product had a copper content of 0.43%.

EXAMPLE 6

Compacted articles were prepared from APS bulk powder and from copper-associated APS both produced as in Example 5. The copper-associated APS was produced using a copper to APS mole ratio of 1.2-1.4:1. The compaction procedure used was generally that described in Example 2, except that 1% sodium palmitate (NaP) or 5% magnesium stearate (MgS) was used as lubricant, except where indicated. A sufficient amount of the somatotropin formulation to give 60 mg and 90 mg doses of somatotropin was placed into a 2.4 mm or 3.2 mm die and compressed at an applied load of 4448 newtons (1000 lbs). These compacted articles were parenterally implanted into commercial-type type crossbred finishing hogs. Average daily weight gain in kg/day (ADG) and feed efficiency (FE), which is defined as daily feed intake divided by ADG (a lower FE is a better FE), and the % improvement in FE of the implanted hogs compared with negative control hogs that received no somatotropin were all determined. These results and the results for a positive control group of hogs, that received daily injections of 2 mg of APS in solution are summarized in Table II. The first stage of the test period was 14 days, followed by a 7 day interim period, followed by a second stage 14 day test period. The results are summarized in Table II.

TABLE II

| | −Control (no treatment) | +Control (2 mg/Day) | Stage 1 Type: Diam: Dose: Lubr: Site: | Cu 3 mm 60 mg NaP Ear | Cu 3 mm 60 mg NaP Fat | APS 3 mm 2 × 30 mg NaP Ear | APS 3 mm 6 × 10 mg NaP[1] Ear |
|---|---|---|---|---|---|---|---|
| ADG (kg) | .98 | 1.11 | | 1.03 | 1.03 | .95 | .87 |
| FE (feed/gain) | 4.10 | 3.24 | | 3.43 | 3.61 | 3.73 | 4.29 |
| % Imp. FE | — | — | | 16.3% | 12.0% | 9.0% | — |

| | −Control (no treatment) | +Control (2 mg/Day) | Stage 2 Type: Diam. Dose: Lubr: Site: | Cu 3 mm 60 mg NaP Ear | Cu 3 mm 60 mg NaP Fat | Cu 2 mm 60 mg NaP[2] Ear | Cu 2 mm 60 mg MgS Ear | Cu 3 mm 90 mg NaP Ear |
|---|---|---|---|---|---|---|---|---|
| ADG (kg) | .90 | 1.02 | | 1.07 | 1.05 | 1.02 | 1.08 | 1.12 |
| FE (feed/gain) | 4.81 | 3.78 | | 3.63 | 3.74 | 3.61 | 3.34 | 3.19 |
| % Imp. FE | — | — | | 24.5% | 22.2% | 25.0% | 30.6% | 33.7% |

[1]10% sodium palmitate
[2]2% sodium palmitate

The implanted articles of the current invention compared favorably to the daily injection and resulted in substantially improved weight gain and feed efficiency compared with the untreated hogs. The 10% level of sodium palmitate resulted in impairment of release of the somatotropin, so that 10% sodium palmitate is higher than an effective amount of the lubricant.

EXAMPLE 7

Compacted articles were prepared from microbially-expressed APS bulk powder which had been isolated and purified as in Example 5. The procedure used was generally that in Example 2, except that 30 mg articles, with a diameter of 6.4 mm were prepared using an applied force of 17,790 newtons (4000 lbs) and 60 mg articles with a diameter of 6.4 mm were prepared using an applied force of 17,790 newtons (4000 lbs). These articles were surgically implanted in the fat in the back of the neck, on the first day of the study. A second set of 3.2 mm diameter articles were prepared at 4448 newtons (1000 lbs) with 30 mg and 60 mg, respectively of somatotropin. These articles were implanted in the fat on the back of the neck with an implant gun. This second set of 3.2 mm articles were implanted on day 15 of the study. The hogs used were commercial-type crossbred finishing hogs, with 10 hogs receiving the 30 mg articles, 10 hogs receiving 60 mg articles, and 10 hogs were control hogs that received sham surgical procedures similar to the treated hogs. ADG, FE and % improvement in FE were determined for the three groups of hogs and are shown in Table III.

TABLE III

| | Control | 30 mg | 60 mg |
|---|---|---|---|
| WEEK 1 | | | |
| ADG (kg) | .87 | .94 | 1.02 |
| FE (feed/gain) | 3.84 | 2.78 | 2.53 |
| WEEK 2 | | | |
| ADG (kg) | .82 | .77 | .67 |
| FE (feed/gain) | 4.27 | 4.62 | 4.58 |
| WEEK 1-2 | | | |
| ADG (kg) | .85 | .85 | .84 |
| FE (feed/gain) | 3.94 | 3.49 | 3.30 |
| % Imp. FE | — | 11.4% | 16.2% |
| WEEK 3 | | | |
| ADG (kg) | .84 | 1.15 | 1.00 |
| FE (feed/gain) | 4.41 | 2.97 | 3.17 |
| WEEK 4 | | | |
| ADG (kg) | .95 | .71 | .62 |
| FE (feed/gain) | 3.95 | 6.70 | 6.31 |
| WEEK 3-4 | | | |
| ADG (kg) | .89 | .93 | .81 |
| FE (feed/gain) | 4.01 | 3.75 | 4.29 |
| % Imp. FE | — | 6.5% | — |
| WEEKS 1-4 | | | |
| ADG (kg) | .87 | .89 | .81 |
| FE (feed/gain) | 3.91 | 3.60 | 3.66 |
| % Imp. FE | — | 7.9% | 6.4% |

These data demonstrate that these compacted articles had an effective prolonged release period of about 1 week. During the second week of each implant cycle, the treated hogs exhibited the expected reduction in feed efficiency usually seen when hogs are withdrawn from administration of somatotropin. Even with these periods of reduced feeding efficiency, both treatment regimens exhibited 7.9% and 6.4% increases in feed efficiency over the 4 week study.

EXAMPLE 8

Compacted somatotropin articles were prepared from MBS prepared as in Example 1. The compacting procedure was as in Example 2, except the tabletting die had a diameter of 3.2 mm and the applied load was 8895 newtons (2000 lbs.). The 50 mg articles were about 5 mm in length. One group of 9 lactating Holstein cows received 2 subcutaneous implantations in the postscapular region of 5 articles each for a total of 500 mg, and a second group of 9 cows received 3 similar implantations for a total of 750 mg. The increase in actual milk production and in 3.5% fat corrected milk production (FC milk) of these treated cows over a group of 10 control cows that received no somatotropin over the 28 days test period and % increase in 3.5% fat corrected milk of the treated cows compared with the control cows are summarized in Table IV.

TABLE IV

| Days/Dose | Increase in Actual Milk (kg/day) | Increase in FC Milk (kg/day) | % Increase in FC Milk |
|---|---|---|---|
| Days 1-14 | | | |
| 500 mg | 4.7 | 5.2 | 19.6% |
| 750 mg | 6.4 | 6.8 | 25.7 |
| Days 15-28 | | | |
| 500 mg | 0.8 | 2.0 | 8.2% |
| 750 mg | 1.1 | 1.0 | 4.1 |

EXAMPLE 9

Compacted somatotropin articles were prepared from MBS prepared as in Example 1, to which 1% magnesium stearate was added as a lubricant. The compacting procedure was as in Example 2, except the tabletting die had a diameter of 4.0 mm, and the applied load was 8895 newtons (2000 lbs.). The 50 mg articles were about 3 mm in length. A group of 10 articles were implanted into a group of 8 lactating Holstein cows, in the postscapular region on day 0 and day 21. The 10 control cows received no somatotropin. During days 1-21, the increase in 3.5% fat corrected milk over the control was 8 5%, and during days 22-42 it was 14.3%. The results of this example were adversely affected by sharp declines in milk production of a number of the cows in the study as they approached the end of the lactation cycle.

EXAMPLE 10

Microbially expressed MBS was prepared and purified essentially as described in Example 1, except as follows. The pH of the concentrated solution of MBS in urea and TRIS was adjusted to a pH of about 10, by addition of NaOH. This solution was diafiltered against 10 volumes of WFI-grade water, with additional NaOH added periodically t maintain the pH at about 10. After diafilteration, the MBS solution was lyophilized and a dry powder was obtained. This product will be referred to as "solution lyophilized MBS".

EXAMPLE 11

Microbially expressed MBS was prepared and purified essentially as described in Example 10, except that the diafiltered MBS solution at pH 10 was neutralized with HCl to precipitate the MBS. The precipitated MBS was lyophilized to produce a dry powder. This product will be referred to as "HCl precipitated MBS".

EXAMPLE 12

Microbially expressed MBS was prepared and purified essentially as described in Example 1, except as follows. The pH of the concentrated solution of MBS in urea and TRIS was adjusted to a pH of about 4 by the addition of $H_3PO_4$. This solution was diafiltered against 10 volumes of WFI-grade water. This diafiltered solution was neutralized with KOH to precipitate the MBS, which was lyophilized to produce a dry powder. This product will be referred to as "KOH precipitated MBS".

EXAMPLE 13

Compacted somatotropin articles were prepared from solution lyophilized MBS prepared as in Example 10 and from HCl precipitated MBS prepared as in Example 11. The compacting procedure was as in Example 2, except that 1% magnesium stearate was added as a lubricant, the diameter of the die was 4 mm and the applied load was 8895 newtons (2000 lbs.). The 50 mg articles were about 3 m in length. One group of 7 Holstein cows received implants of 10 of the 50 mg articles (500 mg total dose) of solution lyophilized MBS and another group of 7 Holstein cows received implants of 10 of the 50 mg articles of HCl precipitated MBS. Implants were subcutaneous in the postscapular region on day 0 and day 21. A group of 7 control cows received sham implantations. The actual milk production and 3.5% fat corrected milk production of the treated cows, compared with control cows that received no somatotropin are shown in Table V.

TABLE V

| Weeks/MBS Type | Increase in Actual Milk (kg/day) | Increase in 3.5 FC Milk (kg/day) | % Increase in 3.5 FC Milk |
|---|---|---|---|
| Weeks 1-3 | | | |
| Soln. Lyo. | 5.3 | 4.9 | 20.6% |
| HCl Precip. | 2.6 | 2.8 | 11.8 |
| Weeks 4-6 | | | |
| Soln. Lyo. | 5.9 | 5.9 | 27.1% |
| HCl Precip. | 2.8 | 3.5 | 16.1 |

Milk production during week 7 showed a slight numerical increase for the solution lyophilized MBS treated cows over the control cows, but no increase was seen with the HCl precipitated MBS.

EXAMPLE 14

A study similar to Example 13 was done, except that 8 Holstein cows received solution lyophilized MBS, 8 Holstein cows received HCl precipitated MBS, 8 Holstein cows received KOH precipitated MBS prepared as in Example 12, and 8 Holstein cows received sham implants. Over the 42 day study milk production of the cows receiving the solution lyophilized MBS exceeded the control cows by 4.5 kg/day, the cows receiving HCl precipitated MBS exceeded the control cows by 4.6 kg/day, and the cows receiving KOH precipitate MBS exceeded the control cows by 4.0 kg/day.

EXAMPLE 15

Compacted articles were prepared from solution lyophilized MBS as in Example 13. A group of 8 Holstein cows received postscapular subcutaneous implantation of 6 of the 50 mg articles (300 mg dose) every 14 days and another group of 8 Holstein cows received 10 of the 50 mg articles (500 mg dose) every 21 days. Over a 42 day study period, the group receiving 300 mg every 14 days showed a milk production increase of 5.4 kg/day over pretreatment milk production of these same cows. Similarly, over a 42 day study period, the group receiving 500 mg every 21 days showed a milk production increase of 5.4 kg/day over pretreatment milk production of these cows.

EXAMPLE 16

Compacted somatotropin articles were prepared from 25 mg of solution lyophilized MBS prepared as described in Example 10. The compaction procedure was similar to Example 2, except the tabletting die had a 2 mm diameter, the applied load was 1112 newtons (250 lbs.), and 1% magnesium stearate was added as a lubricant. Five groups of 9 Holstein cows each received subcutaneous implants in the postscapular region at various doses and various intervals and a group of 9 control cows received sham implants every 14 days. Over the 84 day study, milk production of the cows receiving 100 mg every 14 days exceeded the control cows by 5.6 kg/day; the production of the cows receiving 200 mg every 14 days exceeded the control cows by 6.4 kg/day, the production of the cows receiving 400 mg every 14 days exceeded the control cows by 7.7 kg/day and the production of the cows receiving 600 mg every 21 days exceeded the control cows by 7.9 kg/day.

EXAMPLE 17

Two groups of compacted articles were prepared from solution lyophilized MBS prepared as in Example 10 to which 1% magnesium stearate was added as a lubricant. The compacting procedures were similar to Example 2, except as follows. One set was 25 mg articles, with 2 mm diameter that were compressed with an applied load of 1112 newtons (250 lbs.). The second set was 50 mg articles, with 4 mm diameter that were compressed with an applied load of 4448 newtons (1000 lbs.). One group of 10 Holstein cows received 12 of the 25 mg articles (300 mg) every 14 days. Another group of 10 Holstein cows received 6 of the 50 mg articles (300 mg) every 14 days. A third group of 10 control cows received sham implants every 14 days. The implants were done subcutaneously in the postscapular region. Over the 42 day study, milk production of the cows who received the 25 mg articles exceeded the control cows by 4.2 kg/day, and the production of the cows who received the 50 mg articles exceeded the control cows by 4.3 kg/day. If the first implantation cycle is considered a transition period between an untreated condition and a treated condition, over days 15–42 of the study milk production increases were 5.0 and 5.4 kg/day over the control cows, for those cows receiving the 25 mg articles and the 50 mg articles respectively.

EXAMPLE 18

Microbially expressed ala-val BST was prepared by expression of recombinant DNA, substantially as described in Example 3a of European Patent Application, Publication No. 193,515 published Sept. 3, 1986, which is incorporated herein by reference. The ala-val BST refractile bodies were isolated, solubilized, natured and purified as described in Examples 10 and 1 to result in a solution lyophilized ala-val BST.

EXAMPLE 19

Compacted articles were prepared from solution lyophilized MBS prepared as in Example 10 and from solution lyophilized ala-val BST prepared as in Example 18. Two millimeter articles were prepared as described in Example 16, including 1% magnesium stearate. Four groups of 9 Holstein cows each received subcutaneous implants of solution lyophilized MBS in the postscapular region at the doses and intervals indicated below. One group of 9 Holstein cows received subcutaneous implants of solution lyophilized ala-val BST in the postscapular region with a 250 mg dose implanted at 14 day intervals. One group of 9 cows received subcutaneous implants between the rear legs, midway between the udder and vulva. A group of 9 control cows received a sham implant in the postscapular region at 14 day intervals. After 42 days, the treated cows showed the following increases in milk production over the control cows: 125 mg MBS every 14 days, an increase of 3.1 kg/day; 250 mg MBS every 14 days, an increase of 4.0 kg/day; 250 mg ala-val BST every 14 days, an increase of 6.6 kg/day; 250 mg MBS implanted above the udder every 14 days, 4.4 kg/day; 375 mg MBS every 14 days, an increase of 5.0 kg/day; and 500 mg MBS every 21 days, an increase of 5.8 kg/day. If the first implantation cycle is considered a transition period between an untreated condition and a treated condition, the increases in milk production of treated cows over control cows excluding the first treatment cycle were as follows: 125 mg MBS every 14 days, an increase of 3.7 kg/day; 250 mg MBS every 14 days, an increase of 4.7 kg/day; 250 mg ala-val BST every 14 days, an increase of 7.4 kg/day; 250 mg MBS implanted above the udder every 14 days, an increase of 5.1 kg/day/; 375 mg MBS every 14 days, an increase of 5.5 kg/day; and 500 mg MBS every 21 days, an increase of 6.4 kg/day.

EXAMPLE 20

Compacted articles were prepared from APS bulk powder and from copper-associated APS prepared as in Example 5. The copper-associated APS was produced using a copper to APS mole ratio of about 2:1. The compaction procedure used was generally that described in Example 2 except that 5% magnesium stearate was used as the lubricant. A sufficient amount of the somatotropin formulation to give 60 mg and 90 mg doses was placed in a 2.4 mm or 3.2 mm die and compressed at an applied load of 4448 newtons (1000 lbs.). These articles were implanted in the fat on the back of the neck to groups of 10 commercial-type crossbred hogs at 14 and 21 day intervals. The study lasted 42 days. ADG, FE and % improvement in feed efficiency over the negative control were determined over the 42 day period. The results are shown in Table VI, compared with a negative control that received no somatotropin and a positive control that received daily injection of 2 mg APS in solution. The data show an effective prolonged release of about 1 week, with the expected reduction in feed efficiency after the release period was over. All of the implant regimens over the full 6 week study showed improved feed efficiency over the negative control and most showed a feed efficiency approximately equivalent to the daily injection positive control.

TABLE VI

|  | −Control (no treatment) | +Control (2 mg/ day) | Dose: Interval: Diam: | APS | | | | Cu APS | |
| --- | --- | --- | --- | --- | --- | --- | --- | --- | --- |
|  |  |  |  | 90 mg 3 Wk 3 mm | 60 mg 2 Wk 3 mm | 90 mg 2 Wk 3 mm | 60 mg 2 Wk 2 mm | 90 mg 3 Wk 3 mm | 60 mg 2 Wk 3 mm |
| Week 1 |  |  |  |  |  |  |  |  |  |
| ADG (kg/day) | .99 | 1.33 |  | 1.03 | 1.05 | 1.17 | 1.14 | 1.12 | 1.16 |
| FE (feed/gain) | 3.40 | 2.73 |  | 2.99 | 2.81 | 2.69 | 2.71 | 2.21 | 2.34 |
| Week 2 |  |  |  |  |  |  |  |  |  |
| ADG (kg/day) | .98 | .99 |  | .78 | .80 | .75 | .70 | .62 | .65 |
| FE (feed/gain) | 3.84 | 3.72 |  | 4.57 | 4.46 | 4.50 | 5.25 | 5.21 | 4.96 |
| Week 3 |  |  |  |  |  |  |  |  |  |

TABLE VI-continued

|  | −Control (no treatment) | +Control (2 mg/ day) | Dose: Interval: Diam: | APS 90 mg 3 Wk 3 mm | APS 60 mg 2 Wk 3 mm | APS 90 mg 2 Wk 3 mm | APS 60 mg 2 Wk 2 mm | Cu APS 90 mg 3 Wk 3 mm | Cu APS 60 mg 2 Wk 3 mm |
|---|---|---|---|---|---|---|---|---|---|
| ADG (kg/day) | .99 | 1.13 |  | .82 | 1.01 | 1.16 | 1.19 | .92 | 1.26 |
| FE (feed/gain) | 3.83 | 3.16 |  | 4.00 | 2.84 | 2.76 | 3.05 | 3.90 | 2.58 |
| Week 4 |  |  |  |  |  |  |  |  |  |
| ADG (kg/day) | .84 | 1.01 |  | 1.28 | .95 | .70 | .82 | 1.23 | .71 |
| FE (feed/gain) | 4.62 | 3.74 |  | 3.20 | 4.16 | 5.27 | 4.72 | 2.60 | 5.21 |
| Week 5 |  |  |  |  |  |  |  |  |  |
| ADG (kg/day) | .79 | 1.03 |  | .97 | .93 | 1.04 | 1.05 | .69 | 1.17 |
| FE (feed/gain) | 4.34 | 3.78 |  | 3.94 | 3.70 | 3.39 | 3.64 | 6.08 | 3.16 |
| Week 6 |  |  |  |  |  |  |  |  |  |
| ADG (kg/day) | 1.00 | 1.19 |  | .78 | .99 | 1.06 | 1.03 | .87 | .82 |
| FE (feed/gain) | 3.88 | 3.43 |  | 5.87 | 3.75 | 3.83 | 3.84 | 4.75 | 4.84 |
| Weeks 1-6 |  |  |  |  |  |  |  |  |  |
| ADG (kg/day) | .93 | 1.11 |  | .95 | .96 | .98 | .99 | .91 | .96 |
| FE | 3.98 | 3.34 |  | 3.82 | 3.43 | 3.45 | 3.58 | 3.54 | 3.45 |
| % Imp. FE | — | — |  | 4.0% | 13.8% | 13.3% | 10.1% | 11.1% | 13.3% |

EXAMPLE 21

Compacted articles were prepared from APS bulk powder and copper-associated APS (2:1 mole ratio of copper to APS) having 5% magnesium stearate as lubricant, as in Example 2, except as set forth below. The compacted articles were prepared in 60 mg and 30 mg sizes, with 3.2 mm diameter compacted at 4448 newtons (1000 lbs.) applied load and 4 mm diameter compacted at 8895 newtons (2000 lbs.) applied load. The 4 mm diameter articles had a height approximately equal to their diameter, so that surface area of the cylinder was minimized. One set of 60 mg, 3.2 mm articles and one set of 30 mg, 3.2 mm articles were placed in stretched 2 mm silastic tubing, with no coating on the ends. 60 mg doses were implanted in commercial-type crossbred hogs, in the fat on the back of the neck, at a 4 week interval. The results over a 5 week period are shown on Table VII, compared with control hogs that received no somatotropin. The results of the two groups of hogs that received the implants with silastic tubing demonstrate manipulation of performance by manipulation of the size of the release surface. The hogs receiving 2 of the 30 mg articles had improved performance over the hogs that received 1 of the 60 mg articles. Since they had open ends, the implants of the 30 mg articles had twice the release surface of the 60 mg articles, resulting in the improved performance.

TABLE VII

|  | CONTROL | Type: Dose: Diam: | APS 60 mg 3 mm | APS 60 mg 4 mm | Cu 60 mg 4 mm | Cu* 60 mg 3 mm | Cu* 2-30 mg 3 mm |
|---|---|---|---|---|---|---|---|
| Week 1 |  |  |  |  |  |  |  |
| ADG (kg/day) | .84 |  | 1.03 | 0.94 | .82 | .93 | 0.83 |
| FE (feed/gain) | 4.23 |  | 2.53 | 3.14 | 3.58 | 3.33 | 3.53 |
| Week 2 |  |  |  |  |  |  |  |
| ADG (kg/day) | .95 |  | .63 | .69 | .73 | .65 | .64 |
| FE (feed/gain) | 3.69 |  | 4.44 | 4.64 | 4.08 | 4.92 | 9.79 |
| Week 3 |  |  |  |  |  |  |  |
| ADG (kg/day) | 1.02 |  | 1.05 | .76 | .92 | .81 | .75 |
| FE (feed/gain) | 3.66 |  | 3.50 | 4.09 | 3.44 | 4.19 | 3.97 |
| Week 4 (Hogs reimplanted) |  |  |  |  |  |  |  |
| ADG (kg/day) | .72 |  | .87 | .89 | .74 | .74 | .84 |
| FE (feed/gain) | 5.35 |  | 3.92 | 3.84 | 4.42 | 4.29 | 3.90 |
| Week 5 |  |  |  |  |  |  |  |
| ADG (kg/day) | .83 |  | .82 | .78 | .99 | .78 | .99 |
| FE (feed/gain) | 5.58 |  | 4.15 | 3.89 | 3.15 | 4.16 | 3.30 |
| Weeks 1-5 |  |  |  |  |  |  |  |
| ADG (kg/day) | .87 |  | .88 | .81 | .84 | .78 | .81 |
| FE (feed/gain) | 3.90 |  | 3.53 | 3.65 | 3.55 | 3.98 | 3.65 |
| % Imp. FE | — |  | 9.5% | 6.4% | 9.0% | — | 6.4% |

*in silastic tubing

EXAMPLE 22

Copper-associated APS was prepared by dissolving APS bulk powder prepared as in Example 5 in deionized water at 60 mg/ml. A sufficient amount of 100 mM CuSO₄ solution was added to result in the desired Cu:APS mole ratio. The pH was adjusted to 7 by addition of sulfuric acid to precipitate the somatotropin. The precipitate was isolated and lyophilized. Compacted articles were prepared from these copper-associated somatotropins having the indicated Cu:APS mole ratios. The compaction procedure used was generally that described in Example 2, except that the diameter was 3.2 mm, 5% magnesium stearate was added as a lubricant, the applied load was 4448 newtons (1000 lbs.), and 60 mg and 30 mg of somatotropin was used, as indicated. These articles were implanted every 14 days in the fat at the back of the neck on groups of 10 hogs. The hogs were monitored over a 6 week study period and the results are shown in Table VIII, compared with a negative control that received no somatotropin and a positive control that received a daily injection of APS in solution. The effective duration of each of the treatments varied, but treatments containing the lower ratios of copper had longer effective duration than the treatments containing higher ratios.

TABLE VII

|  | −Control (no treatment) | +Control (2 mg/day) | Dose: Cu:APS: | 60 mg 1:1 | 60 mg 2:1 | 2 × 30 mg 1:1 | 2 × 30 mg 2:1 | 2 × 30 mg 1.5:1 |
|---|---|---|---|---|---|---|---|---|
| Week 1 | | | | | | | | |
| ADG (kg/day) | 1.00 | 1.05 | | 1.05 | 1.01 | .99 | .89 | .92 |
| FE (feed/gain) | 2.83 | 2.73 | | 2.57 | 3.08 | 2.97 | 2.90 | 2.95 |
| Week 2 | | | | | | | | |
| ADG (kg/day) | .79 | .98 | | .86 | .69 | .81 | .87 | .92 |
| FE (feed/gain) | 4.24 | 2.97 | | 3.73 | 4.64 | 3.72 | 3.33 | 3.19 |
| Week 3 | | | | | | | | |
| ADG (kg/day) | .95 | 1.02 | | 1.05 | 1.21 | .91 | 1.00 | 1.07 |
| FE (feed/gain) | 3.36 | 2.76 | | 2.35 | 2.41 | 2.87 | 2.84 | 2.66 |
| Week 4 | | | | | | | | |
| ADG (kg/day) | .99 | 1.13 | | .64 | .70 | .93 | 1.01 | .81 |
| FE (feed/gain) | 3.28 | 2.75 | | 4.69 | 6.71 | 3.32 | 3.24 | 3.90 |
| Week 5 | | | | | | | | |
| ADG (kg/day) | .81 | .97 | | 1.13 | 1.11 | 1.05 | .99 | 1.00 |
| FE (feed/gain) | 3.90 | 3.15 | | 2.40 | 2.95 | 2.58 | 3.16 | 2.94 |
| Week 6 | | | | | | | | |
| ADG (kg/day) | .75 | .68 | | .69 | .69 | .29 | .63 | .38 |
| FE (feed/gain) | 4.23 | 4.16 | | 5.86 | 5.03 | 7.05 | 5.69 | 4.72 |
| Weeks 1–6 | | | | | | | | |
| ADG (kg/day) | .88 | .97 | | .91 | .90 | .83 | .90 | .85 |
| FE (feed/gain) | 3.43 | 2.85 | | 2.88 | 3.31 | 3.17 | 3.23 | 3.38 |
| % Imp. FE | — | — | | 16.0% | 3.5% | 7.6% | 5.8% | 1.5% |

EXAMPLE 23

Compacted articles were produced from APS bulk powder produced as in Example 5, dry blended with a sufficient quantity of CuSO$_4$ to give the indicated Cu to APS mole ratio and from precipitated copper-associated APS with the indicated Cu to APS mole ratio. The compaction procedure was generally as described in Example 2, except that 5% magnesium stearate was added as a lubricant, and the applied load was either 1000 newtons (225 lbs.) or 2224 newtons (500 lbs.), as indicated. The articles were implanted either weekly or every 2 weeks, as indicated, into groups of 10 commercial-type crossbred hogs in the fat on the back of the neck. The results of the study are given in Table IX below.

TABLE IX

| Treatment*: | 1 | 2 | 3 | 4 | 5 | 6 | 7 |
|---|---|---|---|---|---|---|---|
| Week 1 | | | | | | | |
| ADG (kg/day) | .93 | 1.24 | 1.00 | 1.24 | 1.13 | 1.19 | 1.19 |
| FE (feed/gain) | 3.05 | 2.31 | 2.71 | 2.42 | 2.44 | 2.34 | 2.34 |
| Week 2 | | | | | | | |
| ADG (kg/day) | .89 | 1.11 | .88 | 1.05 | .91 | .95 | .84 |
| FE (feed/gain) | 4.19 | 2.76 | 3.28 | 3.17 | 3.60 | 3.17 | 3.62 |
| Week 3 | | | | | | | |
| ADG (kg/day) | .93 | 1.13 | .97 | 1.09 | 1.14 | 1.20 | 1.04 |
| FE (feed/gain) | 3.99 | 2.96 | 3.32 | 3.19 | 3.06 | 2.70 | 3.36 |
| Week 4 | | | | | | | |
| ADG (kg/day) | 1.00 | 1.21 | 1.09 | 1.11 | 1.08 | 1.02 | .94 |
| FE (feed/gain) | 3.31 | 2.83 | 3.08 | 3.40 | 3.27 | 3.62 | 3.83 |
| Week 5 | | | | | | | |
| ADG (kg/day) | 1.02 | 1.18 | 1.12 | 1.21 | 1.02 | 1.08 | 1.30 |
| FE (feed/gain) | 3.54 | 3.11 | 3.08 | 3.08 | 3.37 | 3.12 | 2.68 |
| Week 6 | | | | | | | |
| ADG (kg/day) | .69 | .98 | .75 | 1.01 | .73 | 1.01 | .63 |
| FE (feed/gain) | 5.29 | 4.89 | 4.47 | 4.18 | 6.00 | 4.43 | 7.06 |
| Weeks 1–6 | | | | | | | |
| ADG (kg/day) | .91 | 1.14 | .97 | 1.12 | 1.00 | 1.08 | .99 |
| FE (feed/gain) | 3.63 | 2.93 | 3.23 | 3.15 | 3.35 | 3.07 | 3.32 |
| % Imp. FE | — | — | 11.0% | 13.2% | 7.7% | 15.4% | 8.5% |

*Treatment 1 - negative control, received no somatotropin
Treatment 2 - positive control, received 2 mg/day of APS in solution
Treatment 3 - 21 mg APS administered weekly, no Cu, 2.4 mm diameter, 1000 newtons (225 lbs.)
Treatment 4 - 21 mg APS administered weekly, dry blend, 2:1 ratio Cu:APS, 2.4 mm diameter, 1000 newtons (225 lbs.)
Treatment 5 - 42 mg APS administered biweekly, dry blend, 4:1 ratio Cu:APS, 3.2 mm diameter, 2224 newtons (500 lbs.)
Treatment 6 - 60 mg APS administered biweekly, precipitate, 1:1 ratio Cu:APS, 3.2 mm diameter, 2224 newtons (500 lbs.)
Treatment 7 - 42 mg APS administered biweekly, precipitate, 1:1 ratio Cu:APS, 3 mm diameter, 2224 newtons (500 lbs.)

EXAMPLE 24

Compacted articles were prepared from precipitated copper-associated APS, with a Cu:APS mole ratio of 1:1, prepared as in Example 5 and from a dry blend of CuSO$_4$ and APS bulk powder with a Cu:APS mole ratio of 4:1. The compaction process used was generally that of Example 2, except that the compacted articles contained 14 mg and 21 mg of somatotropin, were 2.4 mm in diameter, contained 5% magnesium stearate lubricant, and were compacted with an applied load of 1000 newtons (225 lbs.). Implantation was weekly, into groups of 10 commercial-type crossbred hogs, in the fat on the back of the neck. The results are shown in Table X, compared with a negative control that received no somatotropin and a positive control that received 2 mg/day of APS administered as a solution.

TABLE X

|  | −Control (no treatment) | +Control (2 mg/day) | Type: CU:APS Ratio: Dose: | Precip 1:1 14 mg | Dry Blend 4:1 21 mg | Dry Blend 4:1 14 mg |
|---|---|---|---|---|---|---|
| Week 1 |  |  |  |  |  |  |
| ADG (kg/day) | 1.23 | 1.15 |  | 1.03 | 1.06 | 1.21 |
| FE (feed/gain) | 2.44 | 2.32 |  | 2.74 | 2.49 | 2.32 |
| Week 2 |  |  |  |  |  |  |
| ADG (kg/day) | 1.08 | 1.00 |  | .91 | .83 | .93 |
| FE (feed/gain) | 3.30 | 3.16 |  | 3.15 | 3.52 | 3.44 |
| Week 3 |  |  |  |  |  |  |
| ADG (kg/day) | 1.02 | 1.05 |  | .96 | 1.01 | 1.00 |
| FE (feed/gain) | 3.47 | 2.64 |  | 3.11 | 2.54 | 3.22 |
| Week 4 |  |  |  |  |  |  |
| ADG (kg/day) | 1.05 | .99 |  | .84 | .79 | .82 |
| FE (feed/gain) | 3.62 | 3.15 |  | 4.02 | 3.89 | 4.34 |
| Week 5 |  |  |  |  |  |  |
| ADG (kg/day) | .78 | .86 |  | .99 | .75 | .84 |
| FE (feed/gain) | 5.22 | 3.49 |  | 3.62 | 4.10 | 4.01 |
| Week 6 |  |  |  |  |  |  |
| ADG (kg/day) | .78 | 1.27 |  | .88 | .99 | 1.02 |
| FE (feed/gain) | 6.45 | 3.32 |  | 4.25 | 4.95 | 3.95 |
| Weeks 1-6 |  |  |  |  |  |  |
| ADG | .99 | 1.05 |  | .93 | .90 | .97 |
| FE (feed/gain) | 3.56 | 2.73 |  | 3.30 | 3.17 | 3.28 |
| % Imp. FE | — | — |  | 7.3% | 11.0% | 7.9% |

EXAMPLE 25

Compacted articles were prepared from a dry blend of APS bulk powder and $CuSO_4$ (2:1 mole ratio Cu:APS) and from copper-associated APS that was prepared by lyophilization of a solution of APS and $CuSO_4$ having a 1:1 mole ratio Cu:APS. The compaction procedure was generally that of Example 2, except that the diameter was 2.4 mm, 5% magnesium stearate was added as a lubricant, the applied load was 1000 newtons (225 lbs.), and 21 mg of somatotropin was used per dose. Implantations were done weekly for 4 weeks into groups of 10 commercial-type crossbred hogs in the fat on the back of the neck. The results are shown in Table XI, compared with a group of negative control hogs that received no somatotropin and a group of positive control hogs that received 2 mg/day of APS in solution. The solution lyophilized 1:1 mole ratio copper-associated APS and the dry blend 2:1 mole ratio performed substantially equivalently.

TABLE XI

|  | −Control (no treatment) | +Control (2 mg/day) | Solution Lyophilized | Dry Blend |
|---|---|---|---|---|
| Week 1 |  |  |  |  |
| ADG (kg/day) | 1.04 | 1.32 | .91 | 1.26 |
| FE (feed/gain) | 2.88 | 1.99 | 2.79 | 2.10 |
| Week 2 |  |  |  |  |
| ADG (kg/day) | .79 | 1.04 | .90 | .79 |
| FE (feed/gain) | 4.09 | 2.84 | 3.22 | 3.59 |
| Week 3 |  |  |  |  |
| ADG (kg/day) | 1.09 | 1.26 | .99 | .96 |
| FE (feed/gain) | 3.18 | 2.47 | 3.16 | 3.26 |
| Week 4 |  |  |  |  |
| ADG (kg/day) | .76 | .59 | .86 | .77 |
| FE (feed/gain) | 4.86 | 3.50 | 3.73 | 3.84 |
| Weeks 1-4 |  |  |  |  |
| ADG (kg/day) | .92 | 1.05 | .91 | .94 |
| FE (feed/gain) | 3.43 | 2.77 | 3.05 | 3.05 |
| % Imp. FE | — | — | 11.1% | 11.1% |

EXAMPLE 26

Compacted articles were produced using a dry blend of $CuSO_4$ and APS bulk powder, at the indicated mole ratios and doses. The compaction procedure was generally that in Example 2, except that 5% magnesium stearate was added as a lubricant, a 2.4 mm die was used and the applied force was 1000 newtons (225 lbs.). These compacted articles were implanted weekly, for a 6 week period into groups of 10 commercial-type crossbred hogs on the back of the neck, just behind the ear. The results of the study are shown in Table XII below, compared with a negative control group that received no somatotropin and a positive control group that received 2 mg/day of APS administered as a solution.

TABLE XII

|  | −Control (no treatment) | +Control (2 mg/day) | Ratio: Dose: | 1:1 21 mg | 2:1 21 mg | 3:1 21 mg | 2:1 17 mg | 2:1 25 mg | 2:1 21 mg |
|---|---|---|---|---|---|---|---|---|---|
| Week 1 |  |  |  |  |  |  |  |  |  |
| ADG (kg/day) | .93 | 1.03 |  | 1.02 | 1.08 | 1.01 | .98 | 1.09 | 1.14 |
| FE (feed/gain) | 3.79 | 3.58 |  | 3.29 | 3.11 | 3.51 | 3.30 | 3.68 | 3.23 |
| Week 2 |  |  |  |  |  |  |  |  |  |
| ADG (kg/day) | 1.00 | 1.20 |  | .98 | .109 | 1.10 | .92 | 1.13 | 1.06 |
| FE (feed/gain) | 3.88 | 3.25 |  | 3.49 | 3.30 | 3.19 | 3.82 | 3.11 | 3.46 |
| Week 3 |  |  |  |  |  |  |  |  |  |
| ADG (kg/day) | .81 | .94 |  | .94 | .79 | .93 | .92 | .97 | 1.01 |
| FE (feed/gain) | 4.71 | 3.97 |  | 3.54 | 4.02 | 3.75 | 3.76 | 3.63 | 3.72 |
| Week 4 |  |  |  |  |  |  |  |  |  |

TABLE XII-continued

| | −Control (no treatment) | +Control (2 mg/day) | Ratio: Dose: | 1:1 21 mg | 2:1 21 mg | 3:1 21 mg | 2:1 17 mg | 2:1 25 mg | 2:1 21 mg |
|---|---|---|---|---|---|---|---|---|---|
| ADG (kg/day) | .86 | 1.01 | | .95 | .90 | 1.01 | .97 | .93 | .89 |
| FE (feed/gain) | 4.56 | 3.72 | | 3.73 | 3.96 | 3.43 | 3.82 | 3.87 | 7.06 |
| Week 5 | | | | | | | | | |
| ADG (kg/day) | .79 | 1.02 | | 1.05 | 1.05 | .94 | .84 | .92 | 1.00 |
| FE (feed/gain) | 5.11 | 3.56 | | 3.61 | 3.75 | 3.98 | 4.63 | 4.23 | 4.16 |
| Week 6 | | | | | | | | | |
| ADG (kg/day) | .87 | 1.06 | | .99 | 1.03 | 1.17 | .97 | 1.23 | 1.09 |
| FE (feed/gain) | 4.55 | 3.73 | | 3.94 | 3.56 | 3.51 | 3.95 | 3.46 | 3.73 |
| Weeks 1-6 | | | | | | | | | |
| ADG (kg/day) | .88 | 1.04 | | .99 | .99 | 1.03 | .93 | 1.05 | 1.03 |
| FE (feed/gain) | 4.29 | 3.56 | | 3.52 | 3.45 | 3.46 | 3.76 | 3.53 | 3.71 |
| % Imp. FE | — | — | | 17.9% | 19.6% | 19.3% | 12.4% | 17.7% | 13.5% |

EXAMPLE 27

Compacted articles were produced from a dry blend of CuSO4 and the APS bulk powder, at a 2:1 mole ratio of Cu:APS. The compaction procedure was generally that of Example 2, except that 5% magnesium stearate or 1% magnesium stearate, as indicated, was added as a lubricant, the applied load was 1000 newtons (225 lbs.) and the diameter was 2.4 mm. Implantations of 21 mg per week were done for 6 weeks into a group of 10 commercial-type crossbred hogs into the neck, directly behind the ear. The results are shown in Table XIII, compared with a negative control group of hogs that received no somatotropin and compared with a positive control group of hogs that received 2 mg of APS per day, administered as a solution. Over the 6 week period of the study, the 1% magnesium stearate and 5% magnesium stearate treatments had similar results.

TABLE III

| | −Control (no treatment) | +Control (mg/day) | 5% MgSt | 1% MgSt |
|---|---|---|---|---|
| Week 1 | | | | |
| ADG (kg/day) | 1.19 | 1.41 | 1.26 | 1.20 |
| FE (feed/gain) | 2.48 | 2.10 | 2.31 | 2.36 |
| Week 2 | | | | |
| ADG (kg/day) | .92 | .97 | .86 | .92 |
| FE (feed/gain) | 3.87 | 3.27 | 3.91 | 4.61 |
| Week 3 | | | | |
| ADG (kg/day) | .92 | 1.03 | .99 | .99 |
| FE (feed/gain) | 4.28 | 2.93 | 3.23 | 6.02 |
| Week 4 | | | | |
| ADG (kg/day) | .72 | 1.13 | .85 | .96 |
| FE (feed/gain) | 3.96 | 3.07 | 3.88 | 3.51 |
| Week 5 | | | | |
| ADG (kg/day) | .81 | 1.05 | 1.03 | .80 |
| FE (feed/gain) | 5.05 | 3.52 | 3.46 | 4.31 |
| Week 6 | | | | |
| ADG (kg/day) | .83 | .96 | .86 | 1.03 |
| FE (feed/gain) | 4.52 | 3.83 | 4.28 | 3.66 |
| Weeks 1-6 | | | | |
| ADG (kg/day) | .90 | 1.09 | .97 | .94 |
| FE (feed/gain) | 3.80 | 2.99 | 3.27 | 3.28 |
| % Imp. FE | — | — | 13.9% | 13.9% |

We claim:

1. A shaped article adapted for parenteral administration of a somatotropin to an animal, comprising an effective dose of a solid somatotropin and an effective amount of a lubricant, which is essentially binder-free, essentially matrix-free, and has at least one uncoated release surface.

2. The article of claim 1 in which the somatotropin is a microbially expressed somatotropin.

3. The article of claim 1 in which the somatotropin is selected from the group consisting of bovine somatotropin and porcine somatotropin.

4. The article of claim 3 in which the somatotropin is microbially expressed bovine somatotropin.

5. The article of claim 4 in which the microbially expressed bovine somatotropin is MBS.

6. The article of claim 4 in which the microbially expressed bovine somatotropin is ala-val BST.

7. The article of claim 3 in which the somatotropin is microbially expressed porcine somatotropin.

8. The article of claim 7 in which the microbially expressed porcine somatotropin is APS.

9. The article of claim 7 in which the microbially expressed porcine somatotropin is copper-associated porcine somatotropin or a dry blend of a copper salt and a porcine somatotropin.

10. The article of claim 9 which has a copper content from about 0.1% to about 3%.

11. A shaped article adapted for parenteral administration of a somatotropin to an animal, comprising
 a. an effective dose of a solid somatotropin, selected from the group consisting of microbially expressed bovine and porcine somatotropin;
 b. an effective amount of a lubricant; and
 c. which is essentially binder-free, essentially matrix-free, and has at least one uncoated release surface.

12. The article of claim 11 in which the lubricant is selected from the group consisting of stearates and palmitates.

13. The article of claim 11 in which the microbially expressed somatotropin is bovine somatotropin.

14. The article of claim 13 in which the microbially expressed bovine somatotropin is MBS.

15. The article of claim 13 in which the microbially expressed bovine somatotropin is ala-val BST.

16. The article of claim 11 in which the microbially expressed somatotropin is a porcine somatotropin.

17. The article of claim 16 in which the microbially expressed porcine somatotropin is APS.

18. The article of claim 16 in which the microbially expressed porcine somatotropin is a copper-associated porcine somatotropin or a dry blend of a copper salt and a porcine somatotropin.

19. A shaped article adapted for parenteral administration of a somatotropin to an animal, consisting essentially of:
 a. an effective dose of a solid somatotropin;
 b. an effective amount of a lubricant; and
 c. optionally, a coating on one or more surfaces of the article, which substantially inhibits release of the somatotropin from the coated surfaces, but with at least one uncoated release surface.

20. The article of claim 19 in which the somatotropin is a microbially expressed somatotropin.

21. The article of claim 19 in which the somatotropin is selected from the group consisting of bovine somatotropin and porcine somatotropin.

22. The article of claim 19 in which the somatotropin is microbially expressed bovine somatotropin.

23. The article of claim 22 in which the microbially expressed bovine somatotropin is MBS.

24. The article of claim 24 in which the microbially expressed bovine somatotropin is ala-val BST.

25. The article of claim 21 in which the somatotropin is microbially expressed porcine somatotropin.

26. The article of claim 25 in which the microbially expressed porcine somatotropin is APS.

27. The article of claim 25 in which the microbially expressed porcine somatotropin is copper-associated porcine somatotropin or a dry blend of a copper salt and a porcine somatotropin.

28. The article of claim 27 which has a copper content from about 0.1% to about 3%.

29. A method of prolonged administration of a somatotropin to an animal, comprising parenteral implantation of a shaped article comprising an effective dose of a solid somatotropin, which is essentially binder-free, essentially matrix-free and has at least one uncoated release surface.

30. The method of claim 29 wherein the somatotropin is a microbially expressed somatotropin.

31. The method of claim 30 wherein the microbially expressed somatotropin is bovine somatotropin.

32. The method of claim 31 wherein the bovine somatotropin is MBS.

33. The method of claim 31 in which the microbially expressed bovine somatotropin is ala-val BST.

34. The method of claim 30 wherein the microbially expressed somatotropin is porcine somatotropin.

35. The method of claim 34 in which the microbially expressed porcine somatotropin is APS.

36. The method of claim 35 wherein the porcine somatotropin is copper-associated porcine somatotropin or a dry blend of a copper salt and a porcine somatotropin.

37. The method of claim 36 wherein the shaped article has a copper content from about 0.1% to about 3%.

38. A method of prolonged administration of a somatotropin to an animal comprising parenteral implantation of a shaped article comprising:
 a. an effective dose of a solid somatotropin selected from the group consisting of microbially expressed bovine and porcine somatotropin;
 b. optionally an effective amount of a lubricant;
 c. optionally a coating on one or more surfaces of the article, which substantially inhibits release of the somatotropin from the coated surfaces; and
 d. which is essentially binder-free, essentially matrix-free and has at least one uncoated release surface.

39. A method of prolonged administration of a somatotropin to an animal, comprising parenteral implantation of a shaped article consisting essentially of:
 a. an effective dose of a solid somatotropin;
 b. optionally, an effective amount of a lubricant; and
 c. optionally, a coating on one or more surfaces of the article, which substantially inhibits release of the somatotropin from the coated surfaces, but with at least one uncoated release surface.

40. The method of claim 39 wherein the somatotropin is a microbially expressed somatotropin.

41. The method of claim 40 wherein the microbially expressed somatotropin is bovine somatotropin.

42. The method of claim 41 wherein the bovine somatotropin is MBS.

43. The method of claim 41 in which the microbially expressed bovine somatotropin is ala-val BST.

44. The method of claim 40 wherein the microbially expressed somatotropin is porcine somatotropin.

45. The method of claim 44 in which the microbially expressed somatotropin is APS.

46. The method of claim 44 wherein the porcine somatotropin is copper-associated somatotropin or a dry blend of a copper salt and a porcine somatotropin.

47. The method of claim 46 wherein the shaped article has a copper content from about 0.1% to about 3%.

48. A method of prolonged administration of a somatotropin to an animal comprising parenteral implantation of a shaped article consisting essentially of
 a. an effective dose of a solid somatotropin selected from the group consisting of microbially expressed bovine and porcine somatotropin;
 b. optionally, an effective amount of a lubricant; and
 c. optionally, a coating on one or more surfaces of the article, which substantially inhibits release of the somatotropin from the coated surfaces, but with at least one uncoated release surface.

* * * * *